(12) United States Patent
Vincent et al.

(10) Patent No.: US 11,342,065 B2
(45) Date of Patent: May 24, 2022

(54) SYSTEMS AND METHODS FOR WORKSTATION RENDERING MEDICAL IMAGE RECORDS

(71) Applicant: FUJIFILM MEDICAL SYSTEMS U.S.A., INC., Morrisville, NC (US)

(72) Inventors: Brigil Vincent, Morrisville, NC (US); Keiji Sugihara, Morrisville, NC (US)

(73) Assignee: FUJIFILM MEDICAL SYSTEMS U.S.A., INC., Morrisville, NC (US)

( * ) Notice: Subject to any disclaimer, the term of this patent is extended or adjusted under 35 U.S.C. 154(b) by 488 days.

(21) Appl. No.: 16/450,477

(22) Filed: Jun. 24, 2019

(65) Prior Publication Data

US 2020/0402645 A1 Dec. 24, 2020

(51) Int. Cl.
*G16H 30/40* (2018.01)
*G16H 30/20* (2018.01)

(52) U.S. Cl.
CPC ............. *G16H 30/40* (2018.01); *G16H 30/20* (2018.01)

(58) Field of Classification Search
CPC .............................. G16H 30/40; G16H 30/20
See application file for complete search history.

(56) References Cited

U.S. PATENT DOCUMENTS

| | | | |
|---|---|---|---|
| 6,895,128 B2 * | 5/2005 | Bohnenkamp | G06F 16/51 382/305 |
| 7,483,557 B2 | 1/2009 | Masuzawa et al. | |
| 7,729,928 B2 | 6/2010 | Backhaus et al. | |
| 7,974,924 B2 | 7/2011 | Holla et al. | |
| 8,028,237 B2 | 9/2011 | Schmitt | |
| 8,316,227 B2 | 11/2012 | Nolan et al. | |
| 8,661,459 B2 | 2/2014 | Gandhi et al. | |
| 8,724,867 B2 | 5/2014 | Koff et al. | |
| 9,501,628 B2 | 11/2016 | Aratsu et al. | |
| 10,015,250 B2 * | 7/2018 | Wenzel | H04L 67/1097 |
| 10,070,839 B2 | 9/2018 | Westerhoff et al. | |
| 10,147,502 B2 | 12/2018 | Paffel et al. | |
| 10,198,816 B2 | 2/2019 | Steigauf et al. | |
| 2007/0011665 A1 | 1/2007 | Gandhi et al. | |
| 2009/0132586 A1 | 5/2009 | Napora et al. | |
| 2016/0210745 A1 | 7/2016 | Yoshida et al. | |
| 2017/0124111 A1 | 5/2017 | Sharma et al. | |
| 2017/0235881 A1 | 8/2017 | Sevenster | |

* cited by examiner

*Primary Examiner* — Eliza A Lam
(74) *Attorney, Agent, or Firm* — Baker Botts L.L.P.

(57) ABSTRACT

A method for transferring and rendering a medical image record, including, receiving, at a workstation of a first user, a subscription to a worklist, the worklist including a Study list having one or more Studies, each Study including at least one Digital Imaging and Communications in Medicine ("DICOM") image; pre-rendering and compressing, by one or more computing devices, at least one DICOM image associated with each Study on the Study list; transferring, from the one or more computing devices to the workstation, one or more pre-rendered and compressed DICOM images; receiving, at the workstation, a request to view at least one pre-rendered and compressed DICOM image; decompressing, at the workstation, at least one requested pre-rendered and compressed DICOM image; rendering, at the workstation, at least one decompressed DICOM image; and displaying at least one rendered DICOM image at the workstation.

18 Claims, 4 Drawing Sheets

SYSTEMS AND METHODS FOR WORKSTATION RENDERING MEDICAL IMAGE RECORDS

BACKGROUND

1. Field of Disclosed Subject Matter

The disclosed subject matter is directed to systems and methods for transferring and rendering digital records, for example, medical image records, and more specifically Digital Imaging and Communications in Medicine ("DICOM") objects. The medical image records can be transferred to and stored at a user's workstation prior to being opened and rendered at the user's workstation.

2. Description of Related Art

In medical imaging, Picture Archiving and Communication Systems ("PACS") are a combination of computers and networks dedicated to the storage, retrieval, presentation, and distribution of images. While images may be stored in a variety of formats, a common format for image storage is DICOM. DICOM is a standard in which, among other things, medical images and associated meta-data can be communicated from imaging modalities (e.g., X-ray, computed tomography ("CT"), and magnetic resonance imaging ("MRI") apparatuses) to the PACS for storage and from PACS to a client device for viewing by a user, such as medical personnel.

Typical PACS viewers use server-side rendering techniques where images can be rendered on a server side based on a real-time request from a user working at a workstation. The images rendered on the server side can be transferred to a user workstation via HyperText Transfer Protocol ("HTTP") channels over a network. Sustainable network connection is required for an acceptable reading experience for the user. As such, in certain scenarios, for example, when a user connects remotely through a relatively slow Virtual Private Network ("VPN") connection, inefficient routing load balancing/routing can occur. Downloading and caching Studies in the workstation when opening the Study can provide an acceptable reading experience for medical personnel, but users still need to wait for the images to be downloaded and cached after opening the Study.

Accordingly, there is a need for systems and methods to create an improved reading experience for users.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter is directed to systems and methods for transferring and rendering a medical image record. For example, a method of transferring a medical image record includes receiving, at a workstation of a first user, a subscription to a worklist, the worklist including a Study list having one or more Studies, each Study including at least one DICOM image. The method includes pre-rendering and compressing, by one or more computing devices, at least one DICOM image associated with each Study on the Study list and transferring, from the one or more computing devices to the workstation, one or more pre-rendered and compressed DICOM images. The method further includes receiving, at the workstation, a request to view at least one pre-rendered and compressed DICOM image; decompressing, at the workstation, at least one requested pre-rendered rendered and compressed DICOM image; rendering, at the workstation, at least one decompressed DICOM image; and displaying at least one rendered DICOM image at the workstation.

Pre-rendering and compressing each DICOM image can occur prior to receiving the subscription. The method can include storing, by the one or more computing devices, at least one pre-rendered and compressed DICOM image.

In accordance with the disclosed subject matter, the method can include querying, by the workstation and to the one or more computing devices, to identify each Study associated with the worklist. The method can include querying, by the workstation and to the one or more computing devices, to identify prior Studies associated with each Study on the Study list, and adding the prior Studies to the Study list. Furthermore, the method can include querying, by the workstation and to the one or more computing devices, to identify each DICOM image associated with each Study on the Study list.

In accordance with the disclosed subject matter, the method can include sending, from the workstation and to the one or more computing devices, a request to pre-render and compress each Study on the Study list. The method can include querying, by the workstation and to the one or more computing devices, to identify a maximum number of parallel channels for transferring the DICOM images. The method can include storing, at the workstation, the pre-rendered and compressed DICOM images.

Compressing at least one DICOM image can include extracting original pixel data from the at least one DICOM image, respectively. Pre-rendering at least one DICOM image can include calculating at least one rendering parameter of the at least one DICOM image, respectively. Pre-rendering and compressing at least one DICOM image can include pre-rendering and compressing at least one original DICOM image. Alternatively or additionally, pre-rendering and compressing at least one DICOM image can include pre-rendering and compressing at least one clinically compressed DICOM image. In accordance with the disclosed subject matter, rendering at least one decompressed DICOM image can include rendering the at least one decompressed DICOM image as a Portable Network Graphic ("PNG") file. Additionally or alternatively, rendering at least one decompressed DICOM images can include rendering the at least one decompressed DICOM image as a Joint Photographic Experts Group ("JPEG") file. The method can include storing, at the workstation, at least one decompressed DICOM image.

As further disclosed herein one or more computer-readable non-transitory storage media embodying software are provided. The software can be operable when executed to receive, at a workstation of a first user, a subscription to a worklist, the worklist including a Study list having one or more Studies, each Study including at least one DICOM image; pre-render and compress, by one or more computing devices, at least one DICOM image associated with each Study on the Study list; transfer, from the one or more computing devices to the workstation, one or more pre-rendered and compressed DICOM images; receive, at the workstation, a request to view at least one pre-rendered and compressed DICOM image; decompress, at the workstation, at least one requested pre-rendered and compressed DICOM image; render, at the workstation, at least one decompressed DICOM image; and displaying at least one rendered DICOM image at the workstation.

As further disclosed herein, a system including one or more processors and a memory coupled to the processors having instructions executable by the processors is provided. The processors can be operable when executing the instructions to receive, at a workstation of a first user, a subscription to a worklist, the worklist including a Study list having one or more Studies, each Study including at least one DICOM image; pre-render and compress, by one or more computing devices, at least one DICOM image associated with each Study on the Study list; transfer, from the one or more computing devices to the workstation, one or more pre-rendered and compressed DICOM images; receive, at the workstation, a request to view at least one pre-rendered and compressed DICOM image; decompress, at the workstation, at least one requested pre-rendered and compressed DICOM image; render, at the workstation, at least one decompressed DICOM image; and displaying at least one rendered DICOM image at the workstation.

DRAWINGS

DETAILED DESCRIPTION

Reference will now be made in detail to the various exemplary embodiments of the disclosed subject matter, exemplary embodiments of which are illustrated in the accompanying drawings. The methods and systems described herein can be used for transferring medical image records, such as medical records stored on a PACS. A variety of records are suitable for retrieval by the present disclosure and the records can be stored in any system, for example a Vendor Neutral Archive ("VNA"). For purpose of illustration and not limitation, the systems and methods are described herein with respect to transferring medical image records (referred to hereinafter as "medical image records" or "records"), specifically DICOM records, stored on a PACS system using DICOM messaging services and DICOM web services, however the methods and system herein can be used for transferring digital records using any transfer protocols. As used in the description and the appended claims, the singular forms, such as "a," "an," "the," and singular nouns, are intended to include the plural forms as well, unless the context clearly indicates otherwise. Accordingly, as used herein, the term medical image record can refer to one medical image record or a plurality of medical image records. For example, and with reference to FIG. 1A for purpose of illustration and not limitation, as referred to herein a medical image record can include a single DICOM Service-Object Pair ("SOP") Instance (also referred to as "DICOM Instance" "DICOM image" and "image") 1 (e.g., 1A-1H), one or more DICOM SOP Instances 1 in one or more Series 2 (e.g., 2A-D), one or more Series 2 inside one or more Studies 3 (e.g., 3A, 3B), and one or more Studies 3.

Figure 1A:
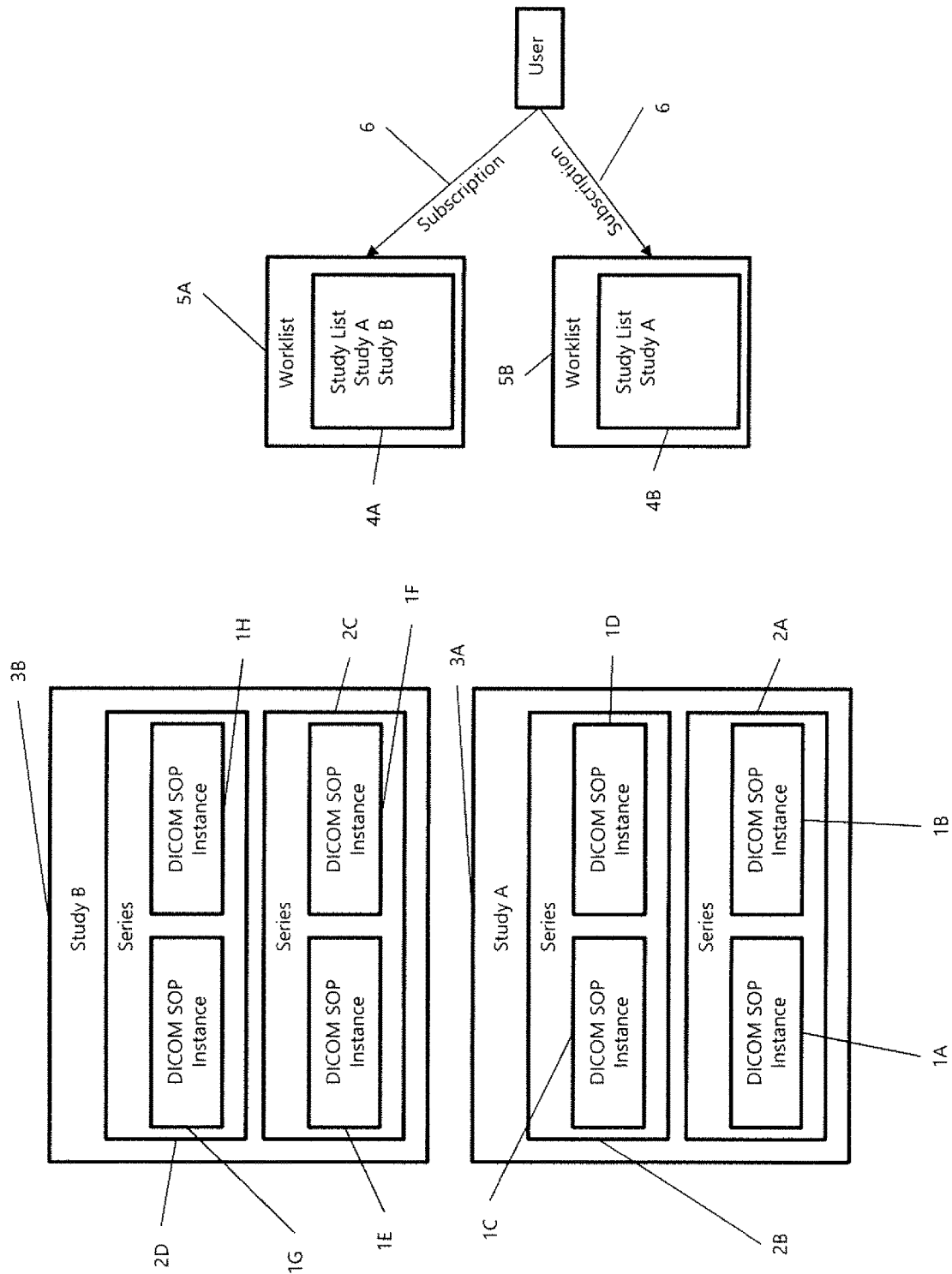
FIG. 1A shows a hierarchy of medical image records that can be transferred in accordance with the disclosed subject matter.
Figure 1B:
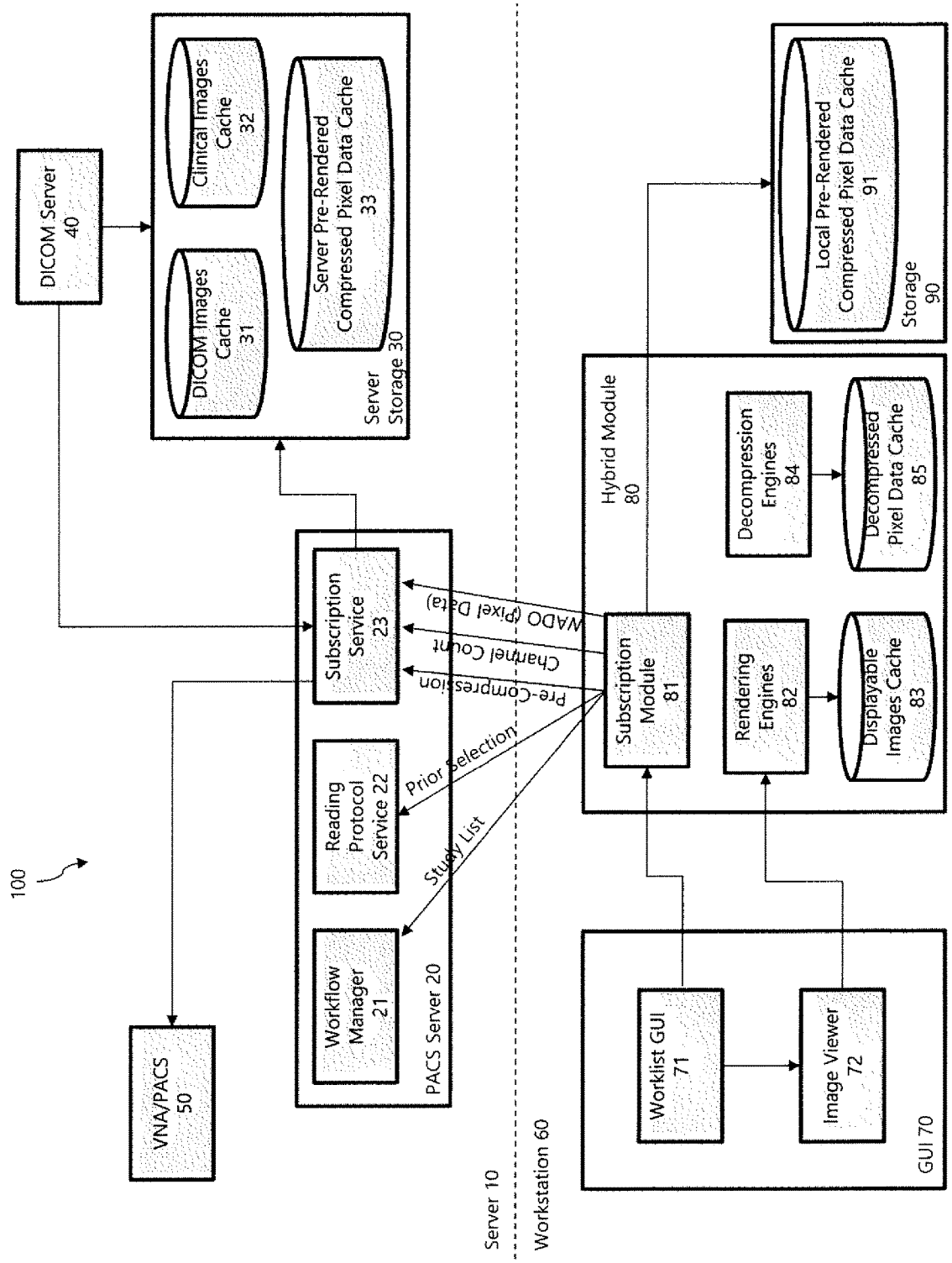
FIG. 1B shows the architecture of a system for transferring and rendering medical image records in accordance with the disclosed subject matter.
Figure 2:
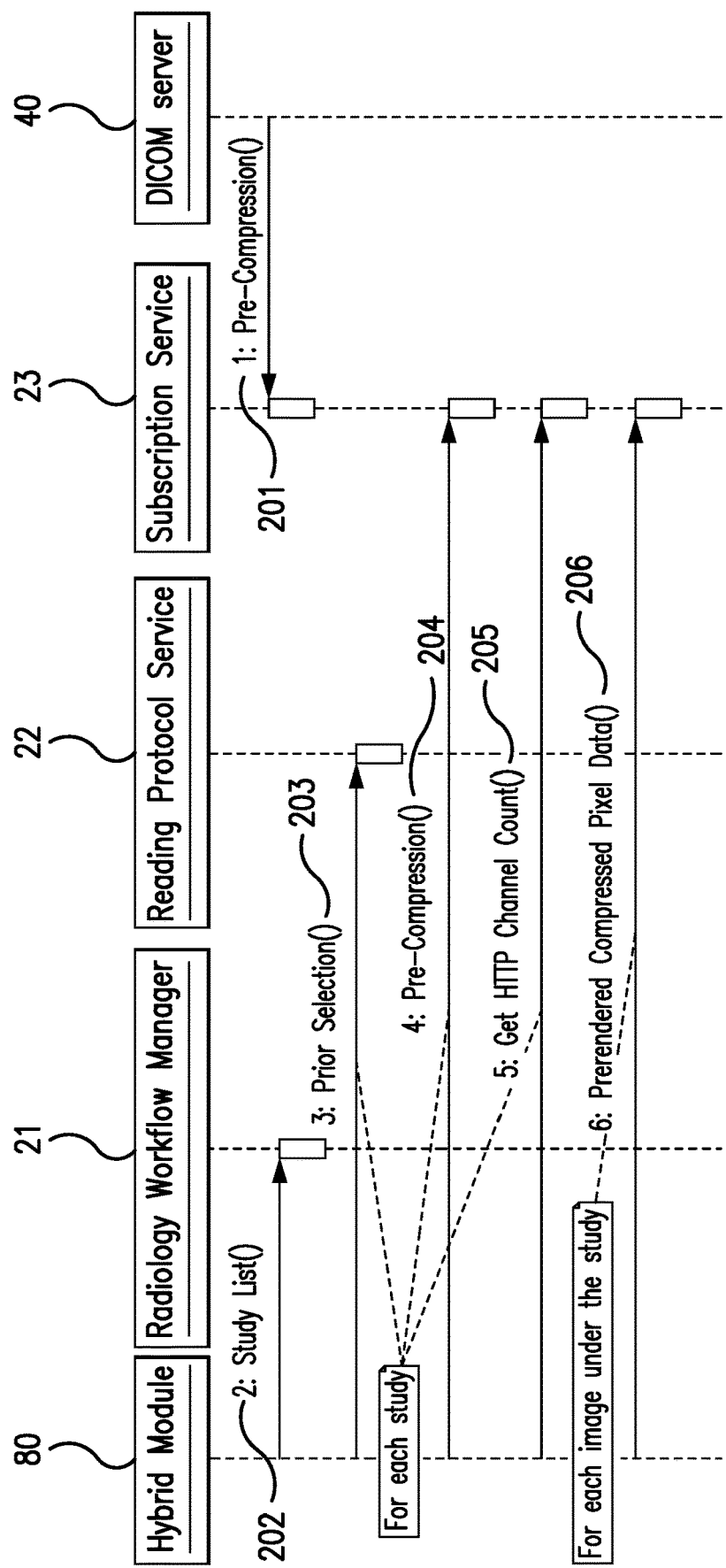
FIG. 2 shows a typical processing flow for transferring and rendering medical image records in accordance with the disclosed subject matter.

Referring to FIGS. 1A, 1B, and 2 for purpose of illustration and not limitation, the disclosed system 100 can include one or more computing devices defining a server side 10 and a user workstation 60 coupled to the one or more computing devices by a network, for example, a Local Area Network ("LAN") connection or VPN connection. The system 100 can be configured to ensure one or more Studies 3 are transferred from the server side 10 to the workstation 60 and cached in the workstation 60 before the user opens the particular Study 3 at the workstation 60. This can provide an improved reading experience in all types of network environments, including on-premise or remote access. The server side 10 can include a PACS server module 20, a server storage 30, a DICOM server 40, and an additional data source, such as a VNA/PACS 50, remote PACS, VNA, or other vendor PACS/VNA. The workstation 60 can include a Graphical User Interface ("GUI") 70, a hybrid module 80, and a storage 90.

A user working at workstation 60 can subscribe 6 to a worklist 5 (e.g., 5A, 5B) using the worklist GUI 71 of the GUI 70. The worklist 5 can include one or more Study lists 4 (e.g., 4A, 4B) including one or more Studies 3. Once subscribed 6, Studies 3 in the subscribed worklist 5 can be transferred from the server side 10 to the workstation 60 and cached in the workstation 60 storage 90. User subscriptions 6 can be stored based on the user and/or the workstation 60 in order to automatically start caching Studies 3 when the user logs into a given workstation 60. Hybrid module 80 running on the workstation 60 can identify and prioritize the Studies 3 to be cached for the user. When the workstation 60 receives a subscription 6 to a worklist 5 (for example when a user logs onto the workstation 60 or when a user newly subscribes in the worklist GUI 71), subscription module 81 can request a Study list 4 from workflow manager 21 on the PACS server 20 for the Studies 3 included in a worklist 5 (see FIG. 2, study list query command 202). Once the Study list 4 is acquired, the Subscription module 81 can start making requests to the subscription service 23 to pre-render and compress images 1 (also referred to as pre-compressed images) of the first Study 3 (see FIG. 2, pre-compression query command 204). The subscription service 81 can then query the reading protocol service 22 to identify prior Studies 3 associated with the first Study 3 (referred to herein as "priors") (see FIG. 2, prior selection query command 203). In order to prepare the list of priors, the Hybrid module 80 can acquire, from the reading protocol service 22, the patient history and then filter out non-relevant priors based on the preference of the user. Priors selected based on information received from the reading protocol service 22 can be added to the Study list 4 to be cached. The process of identifying the relevant priors can be carried out for each of the Studies 3 in the Study list 4. To keep subscription priority synchronized with reading priority, the Study list 4 can be refreshed at intervals based on an interval preference associated with the worklist 5. For example, for an "unread Study" worklist 5, the Study list 4 can refresh every 30 seconds in order to keep the Study list 4 updated with images 1 arriving from the DICOM Server 40 to the PACS server 20. After each refresh, a priority adjustment can be performed in the caching order to ensure that caching will be performed in a desired reading order associated with the worklist 5.

The order of caching can be based on the order of the Studies 3 in the worklist 5. For example, the first Study 3A in the Study list 4A of worklist 5A can be cached first, followed by its priors. After the first Study 3A and its priors are cached, the system 100 can transfer and cache the next Study 3B on the Study list 4A. If a new Study 3 arrives during this ordered processing, the newly arrived Study 3 can be processed by honoring its place in the order, based on the sort criteria of the worklist 5A. The number of priors associated with each Study 3 can be determined by a preference for a user. For example, if a user preference is to compare a Study 3 with its five priors by matching the procedure code, then those priors can be cached along with the Study 3. Preferences can be specific to image type. For example, a user may prefer to see live priors when viewing magnetic resonance images but only two priors when viewing computed tomography images. The user's preferences can be stored by the workstation 60, the worklist 5, or within the reading protocol service 22.

The cache status of each Study 3 can be displayed in the worklist GUI 71, indicating whether each Study 3 in the worklist 5 has been cached at the workstation 60 or not. The user can have the option to unsubscribe from a worklist 5, and that can remove the cached Studies 5 from the workstation 60. Cached Studies 3 can be cleared based on rules set by user preference. For example, the cached Studies 3 can be cleared using any of the following rules: (1) manually cleared by the user; (2) cleared upon the user logging off the workstation 60; (3) cleared upon the user closing the worklist 5; (4) cleared based on a time limit for storage; (5) cleared based on maximum number of Studies 3 to be kept in the cache; or other similar rules.

Caching a Study 3 can include downloading all DICOM images 1 under the Study 3 and storing the downloaded images in Workstation 60 storage 90 for rendering by the workstation 60 hybrid module 80. To identify all DICOM Instances 1 under a Study 3, the subscription module 81 can query the subscription service 23 to collect this information from the PACS data base if the Study 3 is stored in the server storage 30. If the Study 3 is stored in an external storage, such as VNA/PACS 50, the subscription service 23 can query the VNA/PACS 50 to get a list of DICOM Instances 1. The queries can be made using a DICOM messaging protocol or a Web Access for DICOM Objects ("WADO") operation (such as or WADO-RS). Once the list of DICOM Instances 1 is obtained, subscription module 81 can start caching the Study 3 by downloading pre-rendered and compressed pixel data of images 1 in the Study 3 (see FIG. 2, prerendered compressed pixel data query command 206).

The system 100 can support downloading multiple pre-rendered and compressed images 1 at a time in order to utilize the network effectively based on the size of the images 1. The number of parallel downloads can be based on the maximum parallel HTTP channels the workstation 60 can use for caching. The transfer of images 1 can utilize the full network bandwidth, or the subscription service 23 and/or hybrid module 80 can limit network bandwidth utilization with tuning preferences. Subscription modules 81 running on each workstation 60 can acquire recommended HTTP channel counts from the subscription service 23 (see FIG. 2, get HTTP channel count query command 205). The subscription service 23 can keep track of parallel caching activity by multiple workstations 60 to effectively suggest channel count to be used by each workstation 60. The maximum number of HTTP channel count can be configurable in the subscription service 23 to tune network utilization due to Study caching, which can ensure other network sensitive transactions will not get affected by Study caching. Subscription module 81 can query the subscription service 23 for a maximum parallel HTTP channel count before starting to cache each Study 3 or after caching a certain number of images 1 in each Study 3. As an example, the subscription module 81 can query the subscription service 23 for a maximum parallel HTTP channel count after 500 images 1 have been cached. This can allow for changes to network utilization in real time, for example, as new users log on or off of the system, and affect the number of available channels available for each user.

Downloaded pre-rendered and compressed images 1 can be stored in workstation storage 90 at local pre-rendered and compressed pixel data cache 91. The workstation storage 90 and/or local pre-rendered and compressed pixel data cache 91 can be one or a combination of primary memory (e.g., random access memory ("RAM")) and disc memory. For example, workstation 60 can be configured such that when the memory required to cache pre-rendered and compressed images 1 exceeds a specific physical memory pool, the workstation 60 can utilize additional disc space to cache the pre-rendered and compressed images 1.

The content of each image 1 in the local pre-rendered and compressed pixel data cache 91 can be designed to be minimal and secured in order to achieve the following goals: (1) images 1 compressed and small enough to download quickly and efficiently with effective utilization of the network; (2) ensure images 1 stored in the local pre-rendered and compressed pixel data cache 91 are secure; and (3) compression allows relatively quick decompression at the workstation 60 side, particularly considering workstation central processing unit ("CPU") and memory resources can be limited. Accordingly, cached images 1 should be pre-rendered and compressed DICOM pixel data in order to minimize processing required at the workstation 60 as part of rendering the images 1 to obtain displayable images 1. Compression can include extracting original pixel data from DICOM images 1. Pre-rendering can include processing, such as performing fundamental image processing techniques to calculate various rendering parameters in order to minimize processing required at workstation 60. The pre-rendered pixel data can be combined with a fixed 128 byte preamble or metadata. The preamble can include DICOM SOP Instance attributes and pre-rendered attributes which can be utilized by the workstation 60 at the time of rendering the images 1. Pre-rendered and compressed files can be retained in the dedicated server pre-rendered and compressed pixel data cache 33. This can avoid redundant pre-rendering and compression for the same pixel data multiple times for multiple users or a single user that logins in several times, for example, from different workstations 60. Server storage 30 can include DICOM images cache 31, clinical images cache 32, and server pre-rendered and compressed pixel data cache 33.

Pre-rendering and compression can require intensive CPU processing which can increase the time required to cache a Study 3 to workstation 60 because pre-rendered and compressed image pixel data needs to be prepared for each image 1 before downloading the image 1 to the workstation 60. Accordingly, server 10 can perform advanced pre-rendering and compression. When a new Study 3 arrives via DICOM server 40, subscription service 23 of the PACS server 20 can perform pre-rendering and compression in the background and can store the pre-rendered and compressed images 1 in server pre-rendered and compressed pixel data cache 33 (see FIG. 2, advanced pre-compression query command 201). When workstation 60 starts subscribing to a Study 3, subscription module 81 can first send a pre-compression request to subscription service 23 on the server 10. Subscription service 23 can identify pre-rendered and compressed images 1 already available in server pre-rendered and compressed pixel data cache 33 in order to avoid on-the-fly pre-rendering and compression, which can require CPU time. If the requested images 1 are not stored in server pre-rendered and compressed pixel data cache 33, the subscription service 23 can begin pre-rendering and compressing the requested images 1. The pre-rendered and compressed images 1 can then be downloaded to the workstation 60, and can be stored in local pre-rendered and compressed pixel data cache 91.

Pre-rendering and compression can be performed on original DICOM images 1, for example, stored in the DICOM images cache 31 or on clinically compressed versions of the DICOM images 1, for example, stored in the clinical images cache 32. Original DICOM images 1 can have more data, but clinically compressed version of DICOM images 1 can be pre-rendered and compressed more quickly. As such, the source for pre-rendering and compression can be based on a user preference. Additionally, pre-rendering and compression can be performed on data from various sources, for example, server storage 30 or additional data sources, such as a VNA/PACS 50, remote PACS, VNA, or other vendor PACS/VNA.

Pre-rendering and compression can include batch processing through all images 1 of a Study 3, and can be performed in the background with a round robin mechanism. The round robin mechanism can allow every workstation 60 to utilize the advantage of pre-rendering and compression. For example, when multiple workstations 60 send pre-compression requests, round robin based pre-rendering and compression can allow all users to be served with the same priority. Likewise, if one workstation 60 requests multiple Studies 3, in a round robin algorithm the multiple request needs to be processed with the same priority and can depend on the number allowed for parallel processing. The number for parallel processing for pre-rendering and compression can be calculated based on server CPU hardware specifications or can be configurable. It can be configured by a server administrator and/or can be auto-adjusted based on an available number of CPU cores in the server and usage needs based on vertical scalability in the specific system deployment.

When opening a cached Study 3 in the image viewer 72 on workstation 60, image viewer 72 can query hybrid module 80 for rendered images 1 for display. Hybrid module 80 can fetch pre-rendered and compressed DICOM images 1 from local pre-rendered and compressed pixel data cache 91. Decompression engines 84 can decompress the images 1 to decompressed pixel data, and rendering engines 82 can generate a final displayable image 1 which can be displayed in the image viewer 72. The rendering engines 82 can render images 1 at various sizes and/or qualities depending on the needs or preferences of the user. For example, the images 1 can be rendered as PNG files for higher quality viewing or JPEG files for lower quality viewing. When opening a Study 3 that is not cached in the workstation 60, hybrid module 80 can start caching the Study 3 automatically. The image viewer 72 does not require waiting for the caching to finish, and can allow a user to review images 1 in a hybrid approach such that, images 1 which are already cached will be rendered locally by the hybrid module 80 and images 1 not cached in the workstation 60 can be rendered using server-side rendering. Furthermore, additional image processing, for example, if a user edits an image 1, can be performed by the server 10.

Bulk rendering can also be supported by the hybrid module 80 such that image viewer 72 can request bulk rendering for multiple images 1 or all images 1 under a Study 3 or Series 2. Hybrid module 80 can generate displayable images 1 and cache them at displayable images cache 83 so that it can provide displayable images 1 quickly when requested from the image viewer 72. Additionally or alternatively, hybrid module 80 can store decompressed pixel data at decompressed pixel data cache 85. Image viewer 72 can utilize one or both of displayable images cache 83 and decompressed pixel data cache 85 as part of a fast playback case where displayable images 1 can be available while the user is performing fast navigation through DICOM images 1 in the image viewer 72.

Figure 3:
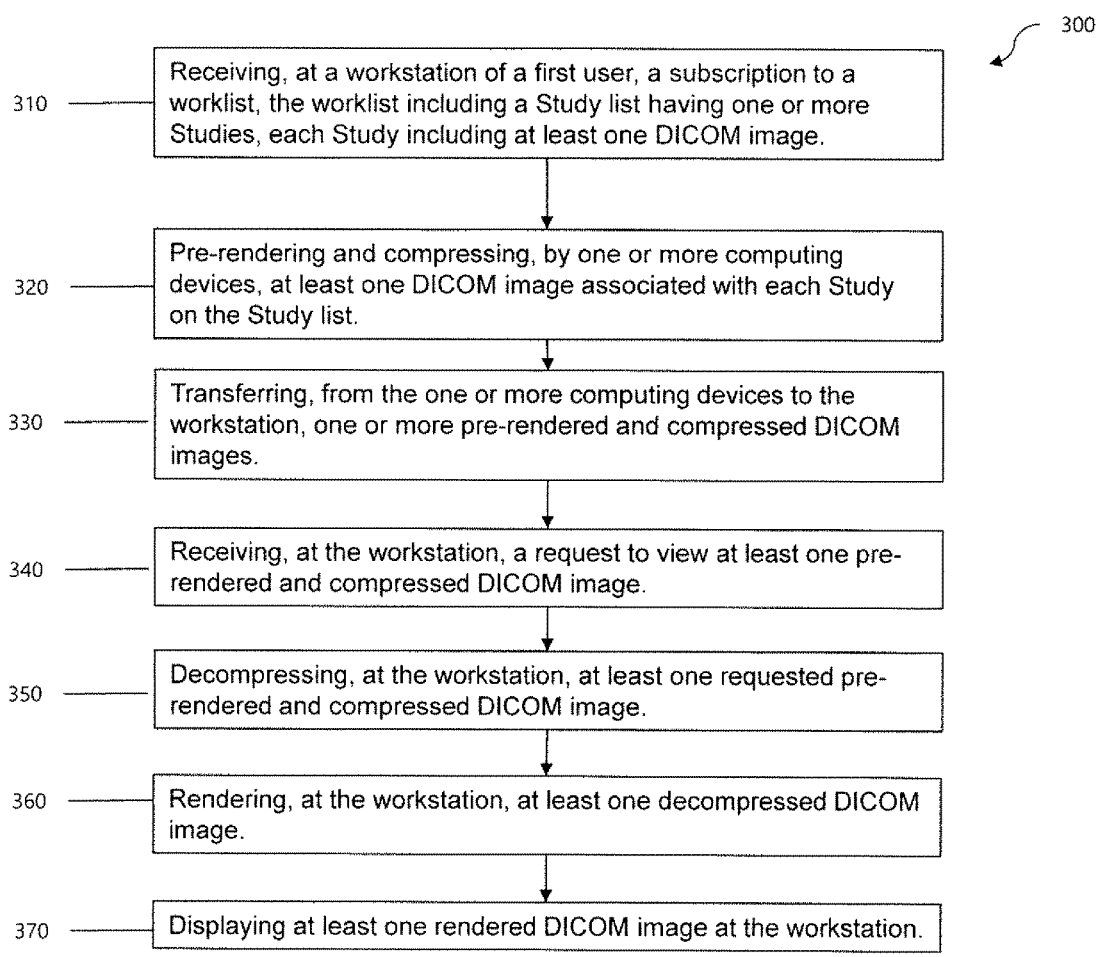
FIG. 3 is a flow chart of a method for transferring and rendering medical image record in accordance with the disclosed subject matter.

FIG. 3 illustrate an example method 300 for transferring and rendering a medical image record. The method can begin at step 310, where the method includes receiving, at a workstation of a first user, a subscription to a worklist, the worklist including a Study list having one or more Studies, each Study including at least one DICOM image. At step 320, the method can include pre-rendering and compressing, by one or more computing devices, at least one DICOM image associated with each Study on the Study list. At step 330, the method can include transferring, from the one or more computing devices to the workstation, one or more pre-rendered and compressed DICOM images. At step 340, the method can include receiving, at the workstation, a request to view at least one pre-rendered and compressed DICOM image. At step 350, the method can include decompressing, at the workstation, at least one requested pre-rendered and compressed DICOM image. At step 360, the method can include rendering, at the workstation, at least one decompressed DICOM image. At step 370, the method can include displaying at least one rendered DICOM image at the workstation. In accordance with the disclosed subject matter, the method can repeat one or more steps of the method of FIG. 3, where appropriate. Although this disclosure describes and illustrates particular steps of the method of FIG. 3 as occurring in a particular order, this disclosure contemplates any suitable steps of the method of FIG. 3 occurring in any suitable order. Moreover, although this disclosure describes and illustrates an example method for transferring and rendering a medical image record including the particular steps of the method of FIG. 3, this disclosure contemplates any suitable method for transferring and rendering a medical image record including any suitable steps, which can include all, some, or none of the steps of the method of FIG. 3, where appropriate. Furthermore, although this disclosure describes and illustrates particular components, devices, or systems carrying out particular steps of the method of FIG. 3, this disclosure contemplates any suitable combination of any suitable components, devices, or systems carrying out any suitable steps of the method of FIG. 3.

As described above in connection with certain embodiments, certain components, e.g., server 10 and workstation 60, can include a computer or computers, processor, network, mobile device, cluster, or other hardware to perform various functions. Moreover, certain elements of the disclosed subject matter can be embodied in computer readable code which can be stored on computer readable media and which when executed can cause a processor to perform certain functions described herein. In these embodiments, the computer and/or other hardware play a significant role in permitting the system and method for displaying medical image records. For example, the presence of the computers, processors, memory, storage, and networking hardware provides the ability to display medical image records in a more efficient manner. Moreover, the display of medical image records, cannot be accomplished with pen or paper, as such information is received over a network in electronic form.

The subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium also can be, or may be included in, one or more separate physical components or media (e.g., multiple compact discs ("CDs"), disks, or other storage devices).

The term "processor" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., a field programmable gate array ("FPGA") or an application-specific integrated circuit ("ASIC"). The apparatus also can include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program can, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA or an ASIC.

Processors suitable for the execution of a computer program can include, by way of example and not by way of limitation, both general and special purpose microprocessors. Devices suitable for storing computer program instructions and data can include all forms of non-volatile memory, media and memory devices, including by way of example but not by way of limitation, semiconductor memory devices, e.g., erasable programmable read-only memory ("EPROM"), electronically erasable programmable read-only memory ("EEPROM"), and flash memory devices; magnetic disks, e.g., internal hard disks or removable disks; magneto-optical disks; and compact disc, read-only memory ("CD-ROM") and digital versatile disc, read-only memory ("DVD-ROM") disks. The processor and the memory can be supplemented by, or incorporated in, special purpose logic circuitry.

Additionally, as described above in connection with certain embodiments, certain components can communicate with certain other components, for example via a network, e.g., a local area network or the internet. To the extent not expressly stated above, the disclosed subject matter is intended to encompass both sides of each transaction, including transmitting and receiving. One of ordinary skill in the art will readily understand that with regard to the features described above, if one component transmits, sends, or otherwise makes available to another component, the other component will receive or acquire, whether expressly stated or not.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A method for transferring and rendering a medical image record, comprising:
  receiving, at a workstation of a first user, a subscription to a worklist, the worklist including a Study list having one or more Studies, each Study including at least one Digital Imaging and Communications in Medicine ("DICOM") image;
  pre-rendering and compressing, by one or more computing devices, at least one DICOM image associated with each Study on the Study list;
  transferring, from the one or more computing devices to the workstation, one or more pre-rendered and compressed DICOM images;
  receiving, at the workstation, a request to view at least one pre-rendered and compressed DICOM image;

decompressing, at the workstation, at least one requested pre-rendered and compressed DICOM image;

rendering, at the workstation, at least one decompressed DICOM image; and displaying at least one rendered DICOM image at the workstation.

2. The method of claim 1, wherein pre-rendering and compressing each DICOM image occurs prior to receiving the subscription.

3. The method of claim 1, further comprising storing, by the one or more computing devices, at least one pre-rendered and compressed DICOM image.

4. The method of claim 1, further comprising querying, by the workstation and to the one or more computing devices, to identify each Study associated with the worklist.

5. The method of claim 1, further comprising querying, by the workstation and to the one or more computing devices, to identify prior Studies associated with each Study on the Study list, and adding the prior Studies to the Study list.

6. The method of claim 1, further comprising querying, by the workstation and to the one or more computing devices, to identify each DICOM image associated with each Study on the Study list.

7. The method of claim 1, further comprising sending, from the workstation and to the one or more computing devices, a request to pre-render and compress each Study on the Study list.

8. The method of claim 1, further comprising querying, by the workstation and to the one or more computing devices, to identify a maximum number of parallel channels for transferring the DICOM images.

9. The method of claim 1, further comprising storing, at the workstation, the pre-rendered and compressed DICOM images.

10. The method of claim 1, wherein compressing at least one DICOM image comprises extracting original pixel data from the at least one DICOM image, respectively.

11. The method of claim 1, wherein pre-rendering at least one DICOM image comprises calculating at least one rendering parameter of the at least one DICOM image, respectively.

12. The method of claim 1, wherein pre-rendering and compressing at least one DICOM image comprises pre-rendering and compressing at least one original DICOM image.

13. The method of claim 1, wherein pre-rendering and compressing at least one DICOM image comprises pre-rendering and compressing at least one clinically compressed DICOM image.

14. The method of claim 1, wherein rendering at least one decompressed DICOM image comprises rendering the at least one decompressed DICOM image as a Portable Network Graphic ("PNG") file.

15. The method of claim 1, wherein rendering at least one decompressed DICOM image comprises rendering the at least one decompressed DICOM image as a Joint Photographic Experts Group ("JPEG") file.

16. The method of claim 1, further comprising storing, at the workstation, at least one decompressed DICOM image.

17. One or more computer-readable non-transitory storage media embodying software that is operable when executed to:

receive, at a workstation of a first user, a subscription to a worklist, the worklist including a Study list having one or more Studies, each Study including at least one Digital Imaging and Communications in Medicine ("DICOM") image;

pre-render and compress, by one or more computing devices, at least one DICOM image associated with each Study on the Study list;

transfer, from the one or more computing devices to the workstation, one or more pre-rendered and compressed DICOM images;

receive, at the workstation, a request to view at least one pre-rendered and compressed DICOM image;

decompress, at the workstation, at least one requested pre-rendered and compressed DICOM image;

render, at the workstation, at least one decompressed DICOM image; and displaying at least one rendered DICOM image at the workstation.

18. A system comprising: one or more processors; and a memory coupled to the processors comprising instructions executable by the processors, the processors being operable when executing the instructions to:

receive, at a workstation of a first user, a subscription to a worklist, the worklist including a Study list having one or more Studies, each Study including at least one Digital Imaging and Communications in Medicine ("DICOM") image;

pre-render and compress, by one or more computing devices, at least one DICOM image associated with each Study on the Study list;

transfer, from the one or more computing devices to the workstation, one or more pre-rendered and compressed DICOM images;

receive, at the workstation, a request to view at least one pre-rendered and compressed DICOM image;

decompress, at the workstation, at least one requested pre-rendered and compressed DICOM image;

render, at the workstation, at least one decompressed DICOM image; and displaying at least one rendered DICOM image at the workstation.

* * * * *